(12) United States Patent
Svetlik

(10) Patent No.: US 8,227,656 B2
(45) Date of Patent: Jul. 24, 2012

(54) WOUND TREATMENT-DRESSING AND METHOD OF MANUFACTURE

(75) Inventor: Harvey E. Svetlik, Grand Prairie, TX (US)

(73) Assignee: Harvey E. Svetlik, Grand Prairie, TX (US)

( * ) Notice: Subject to any disclaimer, the term of this patent is extended or adjusted under 35 U.S.C. 154(b) by 233 days.

(21) Appl. No.: 12/658,530

(22) Filed: Feb. 5, 2010

(65) Prior Publication Data

US 2010/0145247 A1 Jun. 10, 2010

(51) Int. Cl.
*A61F 13/00* (2006.01)

(52) U.S. Cl. ............. 602/48; 602/46; 424/443; 424/449

(58) Field of Classification Search ............... 602/41, 602/42, 46, 48, 52; 604/304–308; 424/447, 424/448, 449
See application file for complete search history.

(56) References Cited

U.S. PATENT DOCUMENTS

| 4,985,467 | A | * | 1/1991 | Kelly et al. | 521/52 |
| 5,858,313 | A | * | 1/1999 | Park et al. | 422/606 |
| 6,361,786 | B1 | * | 3/2002 | Shanbrom | 424/405 |
| 2004/0086549 | A1 | * | 5/2004 | Nielsen | 424/445 |

* cited by examiner

*Primary Examiner* — Kim M Lewis
(74) *Attorney, Agent, or Firm* — Charles D. Gunter, Jr.

(57) ABSTRACT

A wound treatment-dressing is shown which includes a dressing body formed from a medically inert, moisture permeable, urethane open-cell foam which is hydrophilic in nature. The foam body has a foam matrix of interconnected foam cells with cell walls which have incorporated therein a combination of inorganic antimicrobials as active agents, the active agents being incorporated into the foam matrix both topically on a foam cell surface and integrally within the foam cell wall. The antimicrobials are manufactured in a selected particle size range which improves predictability and performance of the wound dressing.

8 Claims, No Drawings

WOUND TREATMENT-DRESSING AND METHOD OF MANUFACTURE

CROSS-REFERENCE TO RELATED APPLICATION

The present application claims priority from a parent application, Ser. No. 11/368,127, filed Mar. 3, 2006, entitled "Wound Dressing and Method of Manufacture," by Harvey E. Svetlik, and from earlier filed provisional application Ser. No. 60/757,170, filed Jan. 6, 2006, entitled "Wound Treatment-Dressing and Method of Manufacture," by Harvey E. Svetlik.

BACKGROUND OF THE INVENTION

1. Field of the Invention

The present invention relates generally to wound dressings such as are useful in treatment of exuding wounds both in first aid as well as longer term treatment situations, particularly where the dressing imparts antimicrobial activity and better than normal accelerated healing to the wound site.

2. Description of the Prior Art

Flexible cellular polyurethane foams are well known and widely used in a variety of industries. These uses range from such things as furniture cushioning and carpet underlayment to cosmetic pads and applicators. Cellular urethane foams have traditionally been prepared using TDI (toluene diisocyanate) polyisocyanate components. In similar fashion, MDI (methylene diisocyanate) has been used to make high density open cell flexible polyurethane foams. These starting materials can be used to manufacture dense foams, i.e., greater than 4.5 lbs./ft$^3$. Various references in the prior art teach the use of resiliently compressible foamed plastic and similar synthetic materials for wound dressings. Such materials can permit comfortable application of pressure even on curved or other non-planar body surfaces.

While the material properties of a foamed plastic may not be critical in the case of cushioning, insulating or packing materials, they are highly critical for purposes of an adequate wound treatment-dressing. For example, it is important or desirable with wound dressings of the type under consideration to have surface properties which for the wound-facing surfaces permit easy flow of moisture into the dressing while avoiding sticking to the wound, and for the outer surface of the dressing to provide at least to a certain extent, a water resistant, breathable barrier. However a number of problems arise in connection with the provision of satisfactory material properties in the context of foam materials of the type under consideration. These problems are discussed in the patent literature and in the relevant technical literature.

For example, British Patent 1417962 describes the use of a non-reticulated polyurethane foam which is modified at the wound-facing inner surface, by application of heat and pressure, to give a layer of collapsed cells, which layer is soft, pliant and facilitates flow of moisture from the wound into the body of the foam material.

A further refinement of such polyurethane foams, involving the use of a body of open-celled hydrophilic foam, is described in WO 92/13576. The addition of an alginate composition to the foam is said to raise the absorptive capacity of the foam and facilitates flow of moisture at a relatively high rate suited to use with very moist wounds.

U.S. Pat. No. 3,903,232 discloses hydrophilic cross-linked polyurethane foams, which are said to be useful for the absorption of body fluids and may be used for external body cleaning, for internal body usage, and as absorptive products such as diapers. The foams are prepared by reacting particular isocyanate-capped polyoxyethylene polyols having an isocyanate functionality greater than 2 with large amounts of an aqueous reactant, preferably water.

EP-A-0335669 discloses a hydrophilic foam composition comprising the "in situ" reaction product of an isocyanate-capped polyether prepolymer, a hydrophilic agent capable of absorbing water, an adjuvant comprising an alcohol, a wetting agent and water. One application which is proposed for the foam composition is in the manufacture of wound dressings. The composition is said to carry the adjuvant releasably, so that at least a portion of the adjuvant is released into an external liquid (e.g. wound exudate) with which the foam composition comes into contact.

U.S. Pat. No. 4,728,323, teaches a method of manufacturing a wound dressing which is comprised of a "substrate" coated with an anticmicrobially effective film of a silver salt. The film is preferably deposited on the substrate by vapor or sputter deposition techniques, as discussed beginning at about column 3, line 30 through line 65. The support sheet with the attached dressing is suspended in a vacuum vessel and all of the air is removed. The material is vaporized by heating to its melting point with an electron beam.

U.S. Pat. No. 4,738,849, teaches a composite wound dressing with separate layers which are subjected to what appears to be a liquid treatment followed by freeze drying.

U.S. Pat. No. 4,997,425, shows a wound dressing which in one embodiment claims to release the antimicrobial little by little (column 4, lines 48-53). As described beginning at column 5, lines 12-20, the antimicrobial solution is poured into a vessel and then subjected to quenching and freezing under vacuum so that a sheet-molded porous layer is produced.

U.S. Pat. No. 5,445,604, shows a wound dressing of multiply layers which includes a "net" in which the strands and junctures are formed integrally during manufacture (column 3, lines 8-10). The reference discusses the use of a hydrophilic polyurethane foam together with a silver salt, e.g., beginning at about column 9, lines 26-65 which discusses "incorporation into the proto-foam prior to polymerization."

U.S. Patent Publication No. 2002/0168400 shows a resin foam wound dressing in which the resin layer has a collagen layer dispersed over the foam layer, following by freeze drying.

U.S. Patent Publication No. 2005/0124724, shows a polymer composition which has a bio-active agent "distributed therein." This reference discusses dispersing metal oxide particles "within the hydrophilic polymer" (paragraph 0052).

Despite the advances in the art represented by references of the above type, a need continues to exist for an improved wound dressing-treatment of the type under consideration.

SUMMARY OF THE INVENTION

It is accordingly an object of the invention to provide an absorbent matrix, treated with an anti-microbial mix, which is processed in a specially designed fashion to produce a wound-treatment dressing of a superior nature to the products presently available in the marketplace.

Another object of the present invention is to provide a wound dressing having at least a wound contacting layer which comprises a uniquely suited absorbent polyurethane foam, and which has a novel combination of active wound treatment-dressing components or agents incorporated therein.

The wound treatment-dressing of the invention provides a new, unique, and novel wound-care treatment, and simultaneously a wound dressing (for humans and animals) which integrates historically proven external, i.e., topically, applied anti-microbial/anti-viral/anti-fungal/anti-anthelmintic medicines with a new delivery system. Together, this combination of features exhibits the improved ability to assist skin and exposed tissue to heal faster and more naturally by preventing and aborting infection, and by actually encouraging tissue growth via increased blood-flow, while noticeably reducing wound pain and discomfort. The preferred product comprises a hydrophilic urethane foam pad dressing which has been specially impregnated with one or more inorganic antimicrobials.

The preferred wound treatment-dressing includes a dressing body having at least a wound contacting surface layer which is formed from a medically inert, moisture permeable, urethane open-cell foam. The foam which makes up at least the wound contacting surface of the dressing body exists as a foam matrix comprised of interconnected foam cells with cell walls which has incorporated therein a combination of inorganic antimicrobials as active agents, the active agents being incorporated into the foam matrix both topically on a foam cell surface and integrally within the foam cell wall.

The preferred active agents are selected from the group consisting of gram positive antimicrobials, gram negative antimicrobials, iodine, and ionic and colloidal silver. Particularly preferred antimicrobials include the combination of gentian-violet, methylene-blue and colloidal or ionic silver. Most preferably, the foam body of the wound treatment-dressing has incorporated therein a zirconium phosphate-based ceramic ion-exchange resin containing silver in the form of silver ions which slowly releases silver ions via an ion exchange mechanism. The preferred foam body has a volume absorbency ratio which is greater than about 20:1 and the gentian-violet and methylene-blue components are present in the foam matrix as nano-sized particles which range in spherical diameter from about 19 microns to 8000 microns. The active agents are at least partially encapsulated within the cell wall surface, which thereby immobilizes the active agent. This can be accomplished during the manufacture of the foam body, wherein a given weight percentage of each antimicrobial agent in the form of particles is physically mixed into the polymer foam ingredients prior to foaming. As the foam body is being formed, the antimicrobials are mechanically included in the foam cell wall upon foaming, whereby some quantity of antimicrobial particles will be totally encapsulated into the wall's polymer structure with the remaining quantity protruding through the polymer wall boundary to be physically exposed into the void space of the open-foam cell.

While a particularly preferred form of the invention utilizes a hydrophilic polyurethane foam as the carrier matrix, it will be appreciated that other absorbent matrixes such as hydrogels, or natural or synthetic fibers or sponges may find utility as well.

Due at least in part to an improved method of manufacture, the pad of the invention functions to protect against and to cleanse the wound of microbes, fungi, infection, providing superior results over presently available wound dressing products.

Additional objects, features and advantages will be apparent in the written description which follows.

DETAILED DESCRIPTION OF THE INVENTION

The preferred antimicrobial polyurethane cellular foam products of the invention are composed of TDI (toluene diisocyanate), pure or polymeric MDI (methylene diisocyanate), TDI/MDI prepolymers, an aqueous component with pure or blended polyols or other foaming agents, and a controlled release antimicrobial agent. The resulting cellular hydrophilic foam products can be used wherever medical wound dressings are required. These products include cosmetic pads, puffs, applicators, foam gauzes, bandages, wipes or any other application requiring the use of cosmetic and medical foam products.

As discussed in the Background portion of the application, various open-cell-structure polymer "foam" membranes are known in the prior art. In many of these prior art products, antimicrobial solutions have been worked into the foam matrix, as by dipping, followed by air drying. Such air-drying deposits small crystals of the antimicrobials onto the surface of the polymer foam's cell wall-structure (resulting in a topical deposition pattern) as the solvent is evaporated. Because the foam pad is resting on a flat surface (typically some sort of support plate) and the air circulation under the pad is restricted, evaporation occurs primarily from the top surface.

So-called "liquid immersion" techniques with air drying are taught in the prior art for manufacturing foams of the general type under consideration. Due to the porosity of the polymer foam membrane, as the liquid solvent is evaporated by air drying from the top surface of the impregnated foam pad, the remaining antimicrobial concentration increases as the solvent evaporates. Gravity draws the more highly concentrated solution to the lower thickness of the foam pad. As a result, as the air drying occurs, the antimicrobial distribution within the polymer membrane is non-uniform, being weakest at the top exposed surface and most concentrated at the bottom surface which is typically in contact with a support plate for the foam pad during the air drying process.

There are a number of properties which distinguish Applicant's foam pads from the prior art of the previously mentioned type. Applicant's preferred foam which is useful for the purposes of the present invention is a medical-grade foam which preferably exhibits volume absorbency greater than a 20:1 ratio, and may range up to a 50:1 ratio. The higher the absorbency ratio, the more body-fluid from the wound can be absorbed, the longer will be the effective use of the wound care pad, the cost per wound healing will be less, and less wound maintenance labor is required.

The preferred foams of the invention are inherently flexible foams. "Hard", stiff foams do not conform to the body. Hard foams that must be wetted to become flexible diminish the function of the wound care pad. These type foams do not absorb the body fluids well and dilute the antibiotic concentration where an antibiotic is the active ingredient or component of the foam. Flexible foams, on the other hand, conform to the body tissue and provide intimate contact for uniform suction of germ infected body fluids by the capillary action of the open-cell polymer foam. Applicant's foams provide conformational area contact over the wound area, without local non-contact, which results are achieved due to the flexibility and thickness of the foam utilized.

Applicant's preferred wound treatment-dressings comprise a dressing body having at least a wound contacting surface layer which is formed from a medically inert urethane open-cell foam. Preferably, the entire dressing body is formed of a hydrophilic polyurethane foam. However, there may be other polymer foams of the same general type, such as open-cell sponge rubber or foamed plastics, which can be impregnated with the active agents to be described, and which may become obvious to others skilled in the art of open-cell foam production. Such open-cell polymer foams are included in the scope of this invention, as well as absorbent fiber materials.

The foam body functions as a liquid absorber in the wound healing process, i.e., liquid exudate from the wound is absorbed into the foam body. The absorbed liquid is retained against free flow out of the dressing but it is kept away from the wound to facilitate healing and tends to evaporate at a controlled rate, as a consequence of the properties of the foam body. These properties also serve to minimize or prevent swelling and avoid excessive moisture retention. The foam body preferably permits slight moisture retention so that it has a reduced tendency to stick to or otherwise interfere with the wound. The controlled flow of liquid from the wound into the foam body can be of importance with regard to wound healing. Flow of liquid should be at a high enough rate to prevent build up of excess liquid at the surface of the wound, but it should not be so high that the wound becomes too dry and the body structure excessively wet. At least the wound contacting layer of the foam body should maintain a very small amount of moisture at the wound surface to provide the wound with a moist healing environment.

The wound dressing-treatment of the invention may be formed in continuous strip or sheet form and may then be cut to give individual dressings of a desired size and shape. For example, a one inch slab of material can be extruded. The top and bottom skin layers can then be cut away leaving a slab of a desired thickness which is allowed to evaporate dry. For example, the slab could be on the order of 1/8 to 1/4 inch thick. While the wound dressing of the invention may be a homogeneous foam body, it will be understood by those skilled in the art that other layers, skins, backings, etc. may be employed with the foam body to form a composite dressing. The wound dressing may be shaped and provided with additional structures or materials such as adhesive portions, as desired and in accordance with the intended use. Thus, for example, the dressing may be oblong with square or rounded corners, tear-drop, circular or oval. The edges of the dressing may be square-cut, rounded, beveled or crimped etc. using a number of methods for example, a heated platen with pressure, high frequency welding/cutting or ultra-sonic welding/cutting.

Preferably a polyether polyurethane foam having the desired hydrophilic characteristics is used for the foam body, or at least the wound contacting layer of the foam body. This kind of foam can be readily absorbent and physiologically compatible to human and animal tissues and can demonstrate good resilience and compressibility suited to the comfortable application of even, sustained pressure. The finished foam body will typically have a thickness in the range of about 2 to 10 mm, preferably about 3 to 7 mm, after drying. A typical useful thickness is 5 mm.

The following examples are intended to illustrate typical hydrophilic polyether foam manufacture techniques but are not intended to be limiting in scope. A variety of polyether polyurethane foam formulations are possible and within the knowledge of those skilled in the art. An objective of the present invention is to provide flexible cellular polyurethane foams that are the reaction product of:

(a) a polyisocyanate component;
(b) an aqueous solution with polyol or polyol blend, and other foaming agents reacted so that the water content is between 5% and 100% water; and
(c) a controlled release antimicrobial in either of the above two components.

The antimicrobial may react with either of the above two components, or be present in its unaltered state. The resultant cellular hydrophilic foam products exhibit antimicrobial properties that are conducive to cosmetic and medical applications.

The polyisocyanate component (a) comprises TDI, monomeric or polymeric MDI or a TDI/MDI prepolymer. These are well known in the art, and include 4,4'-2,4'-, and 2,2' diphenylmethane diisocyanate, various polyphenylenepolymethylene polyisocyanates (polymeric MDI), and mixtures of some or all of these compounds. The polyisocyanate component (a) may also include one or more other aliphatic, cycloaliphatic, arylaliphatic, and/or aromatic polisocyanates. Specific examples of such other polyisocyanates include: alkylene diisocyanates with 4 to 12 carbons in the alkylene radical such as 1,12-dodecane diisocyanate, 2-2ethyl-1,4,tetramethylene diisocyanate and 1,6-hexamethylene diisocyanate; cycloaliphatic diisocyanates such as 1,3-and 1,4-cyclohexane diisocyanate as well as any mixtures of these isomers, 1-isocyanato-3,3,5-trimethyl-5-isocyanatomethylcyclohexane(isophorone diisocyanate), and 2,4- and 2,6-hexahydrotoluene diisocyanate as well as the corresponding isomeric mixtures; and other aromatic polyisocyanates such as 2,4- and 2,6-toluene diisocyanate (TDI) and the corresponding isometric mixtures. The polyisocyanate component((a) should typically contain at least 80% MDI or polymeric MDI.

Frequently, so-called modified multivalent isocyanates, i.e., products obtained by the partial chemical reaction of organic diisocyanates and/or polyisocynanates are used. Examples include diisocyanates and/or polyisocyanates containing ester groups, urea groups, biuret groups, allophanate groups, carbodiimide groups, isocyanurate groups, and/or urethane groups. Specific examples include organic, preferably aromatic polyisocyanates containing urethane groups (also known as isocyanate prepolymers) and having a free NCO content of 20-46 weight percent, preferably 25 to 40 weight percent, based on the total weight, which may be prepared by reacting polyisocyanate with low molecular weight diols, triols, dialkylene glycols, trialkylene glycols, or polyoxyakylene glycols with a molecular weight of up to 8000. Examples of polyols useful for preparing isocyanate prepolymers include diethylene glycol, dipropylene glycol, polyoxyethylene glycol, polyoxypropylene glycol, and polyoxypropylene polyoxyethylene glycols or -triols. Isocyanate prepolymers may optionally be mixed together or mixed with unmodified organic polyisocyanates such as 2,4'- and 4,4' diphenylmethane diisocyanate, polymeric MDI, 2,4- and/or 2,6-toluene diisocyanate.

Crude polyisocyanates may also be used in the compositions of the present invention, such as crude toluene diisocyanate obtained by the phosgenation of a mixture of toluene diamines or crude diphenylmethane diisocyanate obtained by the phosgenation of crude diphenylmethane diamine.

The aqueous component (b) is comprised of water and one or more polyol compounds. Representative polyols, which may be employed in the invention, are well known to those skilled in the art. Representative polyols include polyhydroxy-containing polyesters, polyoxyalkylene polyether polyols, polyhydroxyterminated polyurethane polymers, polyhydroxyl-containing phosphorous compounds, and alkylene oxide adducts of polyhydric polythioesters, polyacetals, aliphatic polyols and thiols, ammonia, and amines including aromatic, aliphatic and heterocyclid amines, as well as mixtures thereof. Alkylene oxide adducts of compounds, which contain two, or more different groups (e.g., amino alcohols) within the above-defined classes may also be used. Generally, the equivalent weight of the polyols will vary from 500 to 10,000, preferably from 750 to 3000.

Any suitable hydroxy-terminated polyester may be used such as can be prepared, for example, from polycarboxylic acids and polyhydric alcohols. Any suitable polycarboxylic acid may be used such as oxalic acid, malonic acid, succinic acid, glutaric acid, adipic acid, pimelic acid, suberic acid, axelaic acid, sebacic acid, maleic acid, fumaric acid, glutaconic acid, terephthalic acid, and the like. Any suitable polyhydric alcohol, including both aliphatic and aromatic may be used such as ethylene glycol, propylene glycol, trimethylene glycol, 1,2-butanediol, 1,3, butanediol, 1,4-butanediol, 1,2-pentanediol, 1,4-pentanediol, 1,5-pentanediol 1,6-hexanediol, 1,7-heptanediol, glycerol, 1,1,1-trimethylolpropane, 1,1,1-trimethylolethane, 1,2,6-hexantriol, alpha-methyl glucoside, pentaerythritol, and sorbitol. Also included within the the term "polyhydric alcohol" are compounds derived from phenol such as 2,2-bis(4-hydroxyphenyl)propane, commonly known as bisphenol A. In order to obtain secondary hydroxyl functional groups, the polyester should be capped with a secondary hydroxyl-containing polyol, such as 1,2-propanediol, 1,3-butanediol, 1,2-butanediol, or similar materials.

Also polyols containing ester groups can be employed in the subject invention. These polyols are prepared by the reaction of an alkylene oxide with an organic dicarboxylic acid anhydride and a compound containing reactive hydrogen atoms. A more comprehensive discussion of these polyols and their preparation can be found in U.S. Pat. Nos. 3,585,185; 3,639,541, and 3,639,542. Although a variety of polyol compounds may be utilized to incorporate secondary hydroxyl groups, such as the above-described polyester polyols, the polyol component is preferably principally composed of polyether polyol(s).

The polyether polyol composition useful in the proactive of the invention contains a predominant amount of secondary hydroxyl groups with a composition consisting of all secondary hydroxyl groups being preferred. Methods of making polyether polyols are well known and include those polyethers prepared from the base catalyzed addition of an alkylene oxide such as ethylene oxide, propylene oxide or butylene oxide, preferably ethylene oxide, to an initiator molecule containing, on the average, two or more active hydrogens. The polyalkylene polyether polyols are well known in the art and may be prepared by any known process.

Examples of initiator molecules are diethylene glycol, ethylene glycol, dipropylene glycol, propylene glycol, trimethylene glycol, 1,2,-butanediol, 1,3-butanediol, 1,4-butanediol, 1,4-pentanediol, 1,5-pentanediol, 1,6-hexanediol, 1,7-heptanediol glycerine, 1,1,1-trimethyolpropane, 1,1,1,-trimethylolethane, 1,2,6-hexantriol, or triethylolpropane. Particularly preferred initiators include trimethylolpropane, glycerine, propylene glycol, and blends of polyoxyalkylene polyether polyols initiated thereby, with glycerine and trimethylolpropane being most preferred. Suitable alkylene oxides include ethylene oxide, propylene oxide, butylenes oxide, amylene oxide, and mixtures of those oxides. A particularly preferred initiator is the reaction product of ethylene oxide or a mixture of ethylene oxide and propylene oxide with one of the aforementioned initiators, followed by capping of the polyether with propylene oxide, to yield a polyether polyol having only predominately secondary hydroxl groups.

The polyol component (b) may also contain solid polymer particles. Preferred polymer particle-containing polyols are the so-called graft polyols comprising a carrier polyol containing predominately secondary hydroxyl groups along with polymer particles. Graft polyols are well known in the art and are typically prepared by the in situ polymerization of one or more vinyl monomers, preferably acrylonitrile and styrene, in the presence of a polyether or polyester polyol, particularly polyols containing a minor amount of natural or induced unsaturation, followed by optional blending with additional liquefied polyol.

The polyurethane foams employed in the present invention are generally prepared by the reaction of a polyoxyalkylene polyether polyol with an organic polyisocyanate in the presence of a blowing agent and optionally in the presence of additional polyhydroxyl-containing components, chain-extending agents, catalysts, surfactants, stabilizers, dyes, fillers and pigments. Chain extending agents include compounds having at least two functional groups bearing active hydrogen atoms such as water, hydrazine, primary and secondary diamines, amino alcohols, amino acids, hydroxy acids, glycols, or mixtures thereof. A preferred group of chain-extending agents includes water, ethylene glycol, 1,4-butanediol and primary and secondary diamines which react more readily with the prepolymer than does water such as phenylene diamine, 1,4-cyclohexane-bis-(methylamine), ethylenediamine, diethylenetriamine, N-(2-hydroxylpropyl)ethylenediamine, N,N'-di(2-hydroxypropyl)ethylenediamine, piperazine, and 2-methylpiperazine.

Suitable catalysts and surfactants, along with typical processes for the preparation of cellular polyurethane foams are disclosed in U.S. Pat. No. Re. 24,514. When water is added to generate $CO_2$ as a blowing agent, corresponding quantities of excess isocyanate to react with the water may be used. It is possible to proceed with the preparation of the polyurethane foams by a prepolymer technique wherein an excess of organic polyisocyanate is reacted in a first step with the polyol of the present invention to prepare a prepolymer having free isocyanate groups, which is then reacted in a second step with water and/or additional polyol to prepare a foam. Alternatively, the components may be reacted in a single working step commonly known as the "one-shot" technique of preparing polyurethane.

The above examples are intended to be merely illustrative of the general class of foams which are suitable for the purpose of practicing the present invention. One particular foam of this general class is commercially available from Lendell Manufacturing Inc., St. Charles, Mich., and sold under the trademark MEDISPONGE™. This particular foam is marketed as a hydrophilic polyether polyurethane foam generated utilizing over 10% water during the foam reaction.

The preferred form of this invention incorporates multiple anti-microbials within the structure of the open cell hydrophilic foam device formed, as described, from the chemical reaction of multivalent isocyanates, namely: TDI (toluene diisocyanate), or monomeric or polymeric MDI (methylene diisocyanate), or TDI/MDI prepolymers, with a sterile aqueous solution incorporating dissolved pure or blended polyols, and/or other foaming agents, and the dissolved (or mixed) blend of multiple antimicrobial agents. The resultant open cellular hydrophilic foam (when cut, packaged and sterilized), is then used as the wound treatment dressing.

In addition to the selection of the preferred class of material for the foam body, the wound dressing-treatment of the invention also involves a particular technique for incorporating multiple active ingredients or components into the foam body which will impart the desired antimicrobial or other desired treatment properties to the ultimate dressing. Applicant's hydrophilic urethane foam pad dressings incorporate one or more inorganic antimicrobials or other active ingredients or components which have been tailored for the particular end application under consideration. The particular antimicrobials or other selected active ingredients can be chosen from among the known agents used for wound treatment.

For example, gentian-violet (hexamethylpararosaniline chloride) is a known inorganic antimicrobial/antifungal, which is widely accepted to kill gram-positive bacteria. Methylene-blue is also a known inorganic antimicrobial/antifungal, widely accepted to kill gram-negative bacteria. Ionic or colloidal silver is a known inorganic antimicrobial/antifungal, widely accepted to kill gram positive and gram negative bacteria. Each of these agents is recognized individually to be a historic antimicrobial and antifungal inorganic chemical agent, but together they can inhibit, and even kill, some viral infections. Applicant's preferred foams utilize a combination of all three of these classes of active agents. When all three components of the preferred wound treatment are used together, the result is a synergistic effect which is greater than the effect of each individual agent acting alone.

Applicant's choice of antimicrobial agent is specifically intended to encompass at least one type of metal, metal oxides, and metal salts, ion-containing particles, or mixtures thereof. The term metal is intended to include any such historically understood member of the periodic chart (including transition metals, such as, without limitation, silver, zinc, copper, nickel, iron, magnesium, manganese, vanadium, gold, cobalt, platinum, and the like, as well as other types including, without limitation, aluminum, tin, calcium, magnesium, antimony, bismuth, and the like). More preferably, the metals utilized within this invention are generally those known as the transition metals. Of the transition metals, the more preferred metals are silver, zinc, gold, copper, nickel, manganese, and iron. Most preferred are silver and zinc. Such metals provide the best overall desired characteristics, such as, preferably, antimicrobial and antifungal characteristics. The preferred form of this invention includes the use of ionic silver. The preferred form of the silver used in this invention is monovalent ionic silver released from silver-sodium-hydrogen-zirconium-phosphate, which is a zirconium-phosphate ceramic ion-exchange resin containing silver.

The preferred form of silver can be provided by incorporating particles of AlphaSan® into the foam body during the foam manufacturing process. AlphaSan® is a zirconium phosphate-based ceramic ion-exchange resin containing silver in the form of silver ions and slowly releases silver ions via an ion exchange mechanism. It is commercially available from Milliken Chemical Company, 920 Milliken Road, Spartenburg, S.C.

Applicant's wound dressing thus preferably includes the use of a plurality of individual antimicrobials/antifungals, including gentian-violet, methylene-blue, iodine, and colloidal and ionic silver, and other such inorganic and organic compounds of the same general type known for their antimicrobial activity. A particular technique of incorporating the active agents into the foam matrix of the foam body is preferred in the practice of the invention. The active agents are preferably introduced into the flexible foam open cell void space so as to coat the cells void space wall, but may also be melded, mixed, dissolved, or otherwise combined into the wall of the polymer structure with a sufficient lower limit of the antimicrobial being exposed from the surface of the foam cell wall (like nugget of gold sticking out of the wall of a mine) into the open cell void-space. This physical arrangement of the active agent more effectively allows the agent to act as an effective antimicrobial upon exposure to the germ infected body fluids absorbed into the open cell by capillary action. Thus, as will be explained in greater detail, the inorganic antimicrobials which are incorporated into the foam bodies of the invention are both on the foam cell surface (topical), and/or within the foam cell wall (integral).

Applicant's preferred manufacturing process provides several unique properties to the ultimately produced foam body. The traditional manufacturing process of topical deposition-drying of antimicrobial onto the walls of the open cell foam structure leaves the antimicrobial "mobile". As a result, currently available wound care dressings of the type under consideration are generally limited to a "single-use" (one-time) application. Washing or rinsing of the pad will dissolve or dilute the residual mobile antimicrobial components. Applicant's manufacturing techniques, on the other hand, result in encapsulation of the antimicrobial into the foam's cell structure and wall, with some antimicrobial particle surface being exposed into the foam cell void, thereby eliminating mobility issues. Applicant's foams are thus distinguishable from the prior art in providing the partial encapsulation of the antimicrobial into the wall surface, which immobilizes the active agent, and thus provides for sterile rinsing and potential re-use where conditions are warranted and allowed.

The pads of the invention are both simultaneously a wound-treatment, and a wound-dressing. The dressings are not a medication or a pain reliever. The dressing itself does not "heal". It is a wound dressing. Healing can only occur if the body systems of the patient are sufficiently healthy to work together and perform their functions, which, over time, is perceived as "wound healing". Without wishing to be bound to a particular theory of operation, a unique aspect of Applicant dressing is to provide an almost immediate environment within which the body's healing processes can proceed unimpeded, giving very rapid growth a few cell-layers at a time. Healthy skin does not experience pain. It is comfortable. When wounded, the nerve ends are exposed to air and infection. The germs "eat" some of the regenerative fluids and proteins, excreting acids and liquids that inflame the nerve ends, sending "pain" signals to the brain. Hence wounds are "painful". The healing is dramatically slowed because the healing "fuel" is being partially consumed by microbes; and the nerve ends are inflamed by their excrement and physical trauma. A small scratch hurts when it is even slightly infected (just slightly red around the scab or wound). In a "room", you can only put so many workers. In a wound, there is only so much "space". The body sends out germ fighters and skin builders. If germs are present, the blood supplies more immune germ fighters and fewer healing proteins.

The dressings of the invention remove the germs and extinguish them in an external killing zone, so there is no need for immune fighters within the wound "room". Now the entire room can be filled with skin growth builders, and all the proteins and fluids that arrive, go directly into skin growth and repair, i.e.: healing. The dressings of the invention maximize the speed at which growth occurs, and minimize the need for immune germ fighters, such that almost immediately, rapid cell growth occurs to cover the "raw", exposed nerve endings. And, the "acidic" excrement from germs is not present to inflame the nerve-ends (exposed at the edge of the wound), so the nerves calm down. Both of these factors combine to give immediate relief from "discomfort" and "pain". The wound is "immediately" covered by just enough regenerative cells to cover the nerve-ends and stop the pain, just like un-wounded healthy skin nerves are presently covered and feel no "pain". The wound is "fed" thru a pipeline carrying regenerative agents (proteins and fluids). At constant flow, when the blood vessel pipeline is carrying both germ fighter agents and healing agents, obviously, not as much healing agent can get through, and, the germs are eating some of the healing agent once it arrives. As a result, the healing goes much slower. When there are no germs, the wound "room" does not call for germ fighters, so at constant flow thru the pipeline, the blood will carry so much more healing agent to the wound; what healing agent arrives then stays; and what stays does not get eaten by germs. The healing effectively proceeds at a faster rate.

What is observed in actual patient use is not actually accelerated healing. What is actually observed is the true capacity of the body to heal itself when not hindered or impeded by the presence of microbe infection. Thus, while Applicant's pads have the capability of achieving the cost benefit of faster healing compared to the norm, they also are enabling the body to heal at its maximum capacity. This is fundamentally different from any bandage presently on the market. By eliminating germs, the body-healing is so fast, that the nerve ends are "immediately" covered and relieved from irritation/inflammation caused by germs and their excrement, such that the "pain" goes away because the skin is returning to its normal condition.

The dressings of the invention effectively act to "clean the wound." Because the germs are removed into the dressing, "pus" (dead germ bodies and their excrement fluids) does not accumulate. In other words, the dressing of the invention acts to prevent wound-surface microbe infection leaving the wound in a natural state of being "clean" in addition to provide auto-debridement.

The wound dressing of the invention inhibits and prevents body fluid evaporation, thus preventing the formation of a "scab". The scab is nature's attempt to form its own bandage, but germ infection can be trapped under the scab, inhibiting healing. The scab inhibits the formation of the new skin epidermis. By preventing scab formation, the epidermis skin growth is not retarded, but is in fact encouraged. By maintaining an proper level of moisture, the new dermal cells will not dry out, leading to scab formation, and will encourage faster dermal growth, due to no competing forces.

A first method of manufacturing the wound dressing-treatment pads of the invention will now be described. The first aspect of the manufacturing technique address the preferred particle size range of the antimicrobial agents which are to be incorporated into the foam body. Both gentian-violet and methylene-blue come in a broad range of non-uniform particle sizes. Applicant's manufacturing technique preferably utilizes specific steps in the manufacture of gentian-violet and methylene-blue particles which produces particles of more uniform particle size, such that they provide more predictable performance.

This is preferably accomplished by first solvating gentian-violet or methylene-blue into a warm solvent at the thermal saturation limit, followed by pressure spraying the concentrated solution through a droplet atomizing nozzle (similar to a perfume-bottle spray nozzle) such that tiny uniform droplets of hot concentrated solution are ejected into a vacuum chamber. The vacuum causes the solvent to "flash" (phase change from a liquid to a gas) leaving tiny, uniform solid crystal particles at the chamber bottom. The solvent gas is then evacuated via the vacuum pump, and the antimicrobial dust is removed by gravity feed through a sealed "star" valve. The result is nano-sized particles of a more uniform spherical diameter.

Applicant's particularly preferred foam bodies have incorporated therein nano-sized particles of a selected particle size range. The application of nano-size-particles in a foam polymer structure requires, for example, a range of spherical diameters from 19 microns to 8000 microns (0.008 inch). This is a preferred particle size range for Applicant's purposes, preferably achieved by the manufacturing process described. However, other processes, such as mechanical pulverizing processes, might also be utilized to generate the above claimed and specified particle size-range forming a part of Applicant's invention.

The gentian-violet, methylene-blue, and also preferably the silver-sodium-hydrogen-zirconium-phosphate particles, are all of a selected uniform size range and controlled in diameter so as to not affect the open-cell foam structure and its resultant capillary absorption ratio. A given weight percentage of each antimicrobial, individually or in permutations and combinations, is physically mixed into the polymer foam ingredients prior to foaming, such that the antimicrobials are mechanically included, similar to a pigment-particle in the foam cell wall upon foaming. Some quantity of antimicrobial particles will be totally encapsulated into the wall's polymer structure. The remaining quantity will protrude through the polymer wall boundary to be physically exposed into the void space of an open-foam cell. Note that the antimicrobial particles are not deposited onto the cell wall, but are physically included within and physically protruding from the cell wall. The antimicrobials are physically captured and are no longer "mobile". This eliminates gross solvation-loss if the pad is washed and re-used again. Applicant's wound dressing-treatments thus provide the possibility (whether eventually used or not) of sterile-rinsing the pad and subsequently re-using the pad, one or more times, without measurable loss of antimicrobial particles. When the prior art foam cell surface deposition-impregnation-drying manufacturing technique is used, significant antimicrobial particle loss occurs upon pad rinsing, because the antimicrobial particles are dissolvable and mobile.

The choice of active ingredients and manufacturing techniques described herein allows the use of gentian-violet, methylene-blue, and silver-sodium-hydrogen-zirconium-phosphate particles individually and in permutations and combinations with each other, in concentrations above the microbial minimum inhibitory concentrations sufficient to kill and/or stop microbe growth. The upper limit for concentrations of each of the above inorganic antimicrobial can be as high as 0.09 grams of each antimicrobial per gram of hydrophilic urethane foam. For each of the above antimicrobials, Applicant's preferred antimicrobial concentrations range from 0.0001% to 9% (gr/gr)by weight.

In one form of the invention, the urethane foam formulations thus allow the solvation of gentian-violet and methylene-blue into one or more of the liquid ingredients used to produce the catalyzed foam. Solid, insolvent particles of antimicrobials, such as the AlphaSan® particles previously described, can also be included by mechanical mixing and suspension of said particulates in the urethane pre-polymer liquid prior to catalization. Upon reaction from a liquid mixture into a solid membrane of an open cell macro-structure, the antimicrobial solution becomes saturated during solidification, and the reformed antimicrobial crystals become encapsulated uniformly throughout the foam, with some crystals exuding or protruding from the foam cell wall to act as the active antimicrobial to the germ-infected body-fluid absorbed into the foam's open cell structure by capillary action.

One particularly preferred formulation comprises the following ingredients on a by-weight basis:

| Weight (lbs) | Ingredient |
| --- | --- |
| 100 | medical grade FDA approved hydrophilic foam |
| 0.21 | Gentian Violet |
| 0.06 | Methylene Blue |
| 0.70. | AlphaSan ® (Milliken chemicals), #RC-2000 |

In the above example, the given respective weight of each antimicrobial agent in the form of particles is physically mixed into the polymer foam ingredients prior to foaming. As the foam body is being formed, the antimicrobials are mechanically included in the foam cell wall upon foaming. Upon completion of the foaming, some quantity of antimicrobial particles are totally encapsulated into the wall's polymer structure with the remaining quantity protruding through the polymer wall boundry to be physically exposed into the void space of the open-foam cell.

An alternative method of manufacturing the pads of the invention may include the steps of forced drying of the wound care pad, immersed and saturated in an antimicrobial solution, by subjecting the "wet" pad to a vacuum. This technique is to be distinguished from the prior art liquid immersion-air drying techniques discussed above. In the forced drying technique, the vacuum increases the effective vapor pressure of the solvent such that it "boils". The solvent is vaporized through the mass of the foam providing for even "drying" and even distribution and dispersion of the antimicrobial through the foam pad. Natural air drying depends upon convection to whisk away the solvent from the exposed open cells of the pad's top surface only. This requires extended time. Vacuum drying solves dispersion and distribution concerns, and accelerates the production efficiency. Additionally, infrared warming of the antimicrobial solution may also be utilized since infrared drying does not heat the surrounding air, but only the material it strikes. Each foam material has an optimum IR absorption frequency. By tuning the IR frequency to that of the solvent, essentially the solvent becomes warmed, thus increasing its vapor pressure, such that in a vacuum, its evaporation rate is further accelerated. Further, the antimicrobial solution should be warmed prior to saturation of the foam pad (within the antimicrobial's upper temperature limit) such that a stronger antimicrobial solution can be formed (like more sugar in boiling water versus cold water), and hence, less solvent is required to be boiled off to achieve the same placement of antimicrobial within the open cell structure.

The preferred manufacturing technique utilizes pre-sterilized ingredients, such that upon direct foaming of the included antimicrobial, the product is itself sterile, is immunized by internal antimicrobials, and is immediately ready for sterile packaging, with or without nuclear irradiation.

Although there are many different varieties of skin wounds, the pressure induced skin ulcer of bed-bound patients is commonly encountered and among the chronic worst wounds.

The charts which follow present evidence of a pressure ulcer timeline to healing at twelve weeks.

| 20040810 Wound 1 | | | | | | | |
| --- | --- | --- | --- | --- | --- | --- | --- |
| Wound Type | Location | Acute Chronic | Stage | Patient Gender | Age | Weeks in Study | Most Current Status |
| Pressure Ulcer | Mid-thoracic | C | 4 | F | 90 | 12.29 | Patient referred to new facility |

Brief Medical History
DOB Apr. 23, 1914
Stage 4 mid-thoracic spine decubitus
Resistant to healing open and clean
Also has Osteoarthritis, Congestive Hear Failure, Atrial Fibrillation and Hypothyroidism

| Date of Treatment | Patient wound history and clinic encounter | Wound Dimensions in cm | | | $cm_3$ Dimensions | Healing % | Number of days Under Treatment |
| --- | --- | --- | --- | --- | --- | --- | --- |
| | | Height | Width | Depth | | | |
| Nov. 02, 2004 | Physician Observation @ 12 weeks | 3.75 | 2.00 | 0.20 | 1.50 | 87.50% | 86 |
| Aug. 10, 2004 | Dressing applied - pushed under superior flap - no pain within 30 seconds | 4.00 | 2.00 | 1.50 | 12.00 | — | — |

* When the wound is flat, but not covered with skin, depth is arbitrarily determined to be 0.01 cm for purposes of $cm_3$ calculation. When wound is covered with new skin the depth is 0.00

| 20040817 Wound 2 | | | | | | | |
| --- | --- | --- | --- | --- | --- | --- | --- |
| Wound Type | Location | Acute Chronic | Stage | Patient Gender | Age | Weeks in Study | Most Current Status |
| Pressure Ulcer | Coccyx | C | 3 | F | 82 | 13.71 | Healed |

Brief Medical History
DOB Oct. 17, 1921
Stage 3 Pressure ulcer, coccyx
Unable to care for self at home - incontinent of stool and urine, but fully alert.
Catherized. Endometrial and Breast CA

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Nov. 16, 2004 | Dressing changes continuing on daily basis due to fecal contamination | 0.25 | 1.00 | 0.01 | 0.25 | 86.67% | 89 |
| Aug. 17, 2004 | RTD Dressing applied | 2.50 | 3.00 | 0.25 | 1.88 | — | — |

* When the wound is flat, but not covered with skin, depth is arbitrarily determined to be 0.01 cm for purposes of $cm_3$ calculation. When wound is covered with new skin the depth is 0.00

20040817 Wound 3

| Wound Type | Location | Acute Chronic | Stage | Patient Gender | Age | Weeks in Study | Most Current Status |
|---|---|---|---|---|---|---|---|
| Pressure Ulcer | Perineal | C | 4 | M | 52 | 10.00 | Healed |

Brief Medical History
DOB Oct. 08, 1963
Paraplegic from gunshot wound at T12 level on 31 Sep. 2001
Admitted because of non-healing sinus tract of at least one-year's duration
in perineal area between anal opening and scrotum. This is near the medial
end of a large right buttock flap scar. Examined first on Aug. 17, 2004.

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Oct. 26, 2004 | Wound healed | 0.00 | 0.00 | 0.00 | 0.00 | 100.00% | 70 |
| Aug. 17, 2004 | Dressing applied at request of patient | 0.50 | 1.50 | 1.50 | 1.13 | — | — |

* When the wound is flat, but not covered with skin, depth is arbitrarily determined to be 0.01 cm for purposes of $cm_3$ calculation. When wound is covered with new skin the depth is 0.00

20040928 Wound 4

| Wound Type | Location | Acute Chronic | Stage | Patient Gender | Age | Weeks in Study | Most Current Status |
|---|---|---|---|---|---|---|---|
| Pressure Ulcer | R Heel | C | 4 | M | 40 | 11.00 | Healed |

| | Brief Medical History DOB Oct. 08, 1963 Paraplegic from gunshot wound at T12 level on 31 Sep. 2001 | | | | | | |
|---|---|---|---|---|---|---|---|
| Date of Treatment | Patient wound history and clinic encounter | Wound Dimensions in cm | | | cm₃ Dimensions | Healing % | Number of days Under Treatment |
| | | Height | Width | Depth | | | |
| Dec. 14, 2004 | Brief clinical history. Base clean good granulation without exudates of breeding | 1.00 | 1.50 | 0.10 | 0.15 | 98.57% | 77 |
| Oct. 26, 2004 | Eschar gone | 3.50 | 3.00 | 1.00 | 10.50 | — | 28 |
| Sep. 28, 2004 | Dressing applied at request of patient | 7.00 | 3.50 | eschar | — | — | — |

* When the wound is flat, but not covered with skin, depth is arbitrarily determined to be 0.01 cm for purposes of cm₃ calculation. When wound is covered with new skin the depth is 0.00

| 20040928 Wound 5 | | | | | | | |
|---|---|---|---|---|---|---|---|
| Wound Type | Location | Acute Chronic | Stage | Patient Gender | Age | Weeks in Study | Most Current Status |
| Pressure Ulcer | R Ankle Lateral Malleolus | C | 3 | M | 40 | 8.00 | Healed |

| | Brief Medical History DOB Oct. 08, 1963 Paraplegic from gunshot wound at T12 level on 31 Sep. 2001 | | | | | | |
|---|---|---|---|---|---|---|---|
| Date of Treatment | Patient wound history and clinic encounter | Wound Dimensions in cm | | | cm₃ Dimensions | Healing % | Number of days Under Treatment |
| | | Height | Width | Depth | | | |
| Nov. 23, 2004 | Healed | 0.00 | 0.00 | 0.00 | 0.00 | 100.00% | 56 |
| Sep. 28, 2004 | Dressing applied at request of patient | 2.00 | 2.00 | 0.25 | 1.00 | — | — |

* When the wound is flat, but not covered with skin, depth is arbitrarily determined to be 0.01 cm for purposes of cm₃ calculation. When wound is covered with new skin the depth is 0.00

| 20050118 Wound 6 | | | | | | | |
|---|---|---|---|---|---|---|---|
| Wound Type | Location | Acute Chronic | Stage | Patient Gender | Age | Weeks in Study | Most Current Status |
| Pressure Ulcer | R Ankle Malleolus | C | 3 | F | 68 | 12.14 | Healed |

| | Brief Medical History |
|---|---|
| | DOB May 29, 1936 |
| | Schizophrenia, paranoid, mixed. Dementia secondary to brain injury. Hypothyroid. Dementia with minimal language ability. Incontinent x2. For about 3-4 weeks she has had a worsening right later maleolar ulcer despite standard treatments. |

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Mar. 22, 2005 | Speckled scabbing - no depth - healed | 0.00 | 0.00 | 0.00 | 0.00 | 100.00% | 63 |
| Jan. 18, 2005 | Inflammation surrounding ulcer-based cleaned | 1.00 | 0.50 | 0.25 | 0.13 | — | — |

* When the wound is flat, but not covered with skin, depth is arbitrarily determined to be 0.01 cm for purposes of cm₃ calculation. When wound is covered with new skin the depth is 0.00

| 20050317 Wound | | | | | | | |
|---|---|---|---|---|---|---|---|
| Wound Type | Location | Acute Chronic | Stage | Patient Gender | Age | Weeks in Study | Most Current Status |
| Pressure Ulcer | Sacral | C | 3 | F | 48 | 12.00 | Continuing |

| | Brief Medical History |
|---|---|
| | DOB Apr. 12, 1957 |
| | Morbidly obese Jan. 10, 2004 231 Jan. 03, 2005 249.8 Jun. 04, 2005 279.3 with diabetes-incontinent of stool - brain damage from auto accident 12 years ago - unable to walk |

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Jun. 08, 2005 | Treatment continuing | 3.00 | 1.00 | 0.20 | 0.60 | 54.89% | 84 |
| Mar. 17, 2005 | RTD applied | 1.90 | 0.50 | 1.40 | 1.33 | — | — |

* When the wound is flat, but not covered with skin, depth is arbitrarily determined to be 0.01 cm for purposes of cm₃ calculation. When wound is covered with new skin the depth is 0.00

| 20050317 Wound 8 | | | | | | | |
|---|---|---|---|---|---|---|---|
| Wound Type | Location | Acute Chronic | Stage | Patient Gender | Age | Weeks in Study | Most Current Status |
| Pressure Ulcer | Coccyx | C | 4 | F | 80 | 12.14 | Treatment Continuing |

Brief Medical History
DOB Oct. 19, 1924
Has diabetes and dementia. Sacral pressure ulcer opening 0.9 and
depth 3.0 Edges tunnel upward 2.7 to 3.5 to R 4.5 and L 2.3

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Jun. 15, 2005 | Treatment continuing | 0.75 | 0.75 | 2.50 | 1.41 | 42.13% | 85 |
| Mar. 17, 2005 | Discussed wound care strategy | 0.90 | 0.90 | 3.00 | 2.43 | — | — |

\* When the wound is flat, but not covered with skin, depth is arbitrarily determined to be 0.01 cm for purposes of cm₃ calculation. When wound is covered with new skin the depth is 0.00

20050323 Wound 9

| Wound Type | Location | Acute Chronic | Stage | Patient Gender | Age | Weeks in Study | Most Current Status |
|---|---|---|---|---|---|---|---|
| Pressure Ulcer | L Leg Lateral | C | 1 | F | 60 | 3.14 | Healed |

Brief Medical History
DOB Oct. 08, 1944
Admitted for pressure ulcers and dehydration plus cellulitis

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Apr. 14, 2005 | healed | 0.00 | 0.00 | 0.00 | 0.00 | 100.00% | 22 |
| Apr. 23, 2005 | RTD applied | 7.00 | 5.50 | 0.01 | 0.39 | — | — |

\* When the wound is flat, but not covered with skin, depth is arbitrarily determined to be 0.01 cm for purposes of cm₃ calculation. When wound is covered with new skin the depth is 0.00

20050408 Wound 10

| Wound Type | Location | Acute Chronic | Stage | Patient Gender | Age | Weeks in Study | Most Current Status |
|---|---|---|---|---|---|---|---|
| Pressure Ulcer | L Leg Anterior | C | 2 | F | 100 | 11.71 | Healed |

Brief Medical History
DOB Jul. 11, 1905
R leg ulcer anterior above ankle

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Jun. 29, 2005 | Wound is dry patient on ten day course of levaquin-no dressing needed-healed | 0.00 | 0.00 | 0.00 | 0.00 | 100.00% | 82 |
| Apr. 08, 2005 | RTD applied | 2.50 | 2.50 | 0.20 | 1.25 | — | — |

\* When the wound is flat, but not covered with skin, depth is arbitrarily determined to be 0.01 cm for purposes of cm₃ calculation. When wound is covered with new skin the depth is 0.00

20050419 Wound 11

| Wound Type | Location | Acute Chronic | Stage | Patient Gender | Age | Weeks in Study | Most Current Status |
|---|---|---|---|---|---|---|---|
| Pressure Ulcer | L Heel | C | 3 | F | 94 | 3.86 | Healed |

Brief Medical History
DOB Sep. 25, 1910

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Jun. 29, 2005 | Healed | 0.00 | 0.00 | 0.00 | 0.00 | 100.00% | 27 |
| Apr. 19, 2005 | 5 months treatment with Aquacel AG, no progress | 1.75 | 0.75 | 0.30 | 0.39 | — | — |

\* When the wound is flat, but not covered with skin, depth is arbitrarily determined to be 0.01 cm for purposes of cm₃ calculation. When wound is covered with new skin the depth is 0.00

20050419 Wound 12

| Wound Type | Location | Acute Chronic | Stage | Patient Gender | Age | Weeks in Study | Most Current Status |
|---|---|---|---|---|---|---|---|
| Pressure Ulcer | L Heel | C | 3 | F | 83 | 11.86 | Healed |

Brief Medical History
DOB Oct. 17, 1921
Unable to care for self at home

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Jul. 11, 2005 | Healed - Eucerin cream only | 0.00 | 0.00 | 0.00 | 0.00 | 100.00% | 83 |
| Apr. 19, 2005 | RTD placed | 1.60 | 1.60 | 0.50 | 1.28 | — | — |

* When the wound is flat, but not covered with skin, depth is arbitrarily determined to be 0.01 cm for purposes of cm₃ calculation. When wound is covered with new skin the depth is 0.00

20050408 Wound 13

| Wound Type | Location | Acute Chronic | Stage | Patient Gender | Age | Weeks in Study | Most Current Status |
|---|---|---|---|---|---|---|---|
| Pressure Ulcer | Coccyx | C | 4 | M | 52 | 6.29 | Patient deceased Jun. 18, 2005 |

Brief Medical History
DOB Nov. 01, 1952
Copd and ms flection contractures arms and legs w/o much movement Rb

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| | Patient deceased Jun. 18, 2005 | | | | | | |
| Jun. 06, 2005 | Fouled with feces | 0.80 | 1.00 | 0.10 | 0.08 | 97.16% | 44 |
| Apr. 19, 2005 | RTD applied | 2.25 | 2.50 | 0.50 | 2.81 | — | — |

* When the wound is flat, but not covered with skin, depth is arbitrarily determined to be 0.01 cm for purposes of cm₃ calculation. When wound is covered with new skin the depth is 0.00

20050419 Wound 14

| Wound Type | Location | Acute Chronic | Stage | Patient Gender | Age | Weeks in Study | Most Current Status |
|---|---|---|---|---|---|---|---|
| Pressure Ulcer | R Buttocks | C | 4 | M | 52 | 6.29 | Patient deceased Jun. 18, 2005 |

| | Brief Medical History DOB Nov. 01, 1952 Copd and ms flection contractures arms and legs w/o much movement Rb | | | | | | |
|---|---|---|---|---|---|---|---|
| Date of Treatment | Patient wound history and clinic encounter | Wound Dimensions in cm Height | Width | Depth | cm₃ Dimensions | Healing % | Number of days Under Treatment |
| | | Patient deceased Jun. 18, 2005 | | | | | |
| Jun. 06, 2005 | Treatment continuing | 3.50 | 3.90 | 0.10 | 1.37 | 92.82% | +44 |
| Apr. 19, 2005 | RTD applied | 4.75 | 4..00 | Eschar | 19.00 | — | — |

*When the wound is flat, but not covered with skin, depth is arbitrarily determined to be 0.01 cm for purposes of cm₃ calculation. When wound is covered with new skin the depth is 0.00

| 20050419 Wound 15 | | | | | | | |
|---|---|---|---|---|---|---|---|
| Wound Type | Loca-tion | Acute Chronic | Stage | Patient Gender | Age | Weeks in Study | Most Current Status |
| Pressure Ulcer | L Calf | A | 2 | F | 63 | 9.86 | In process |

| 20050423 Wound 17 | | | | | | | |
|---|---|---|---|---|---|---|---|
| Wound Type | Loca-tion | Acute Chronic | Stage | Patient Gender | Age | Weeks in Study | Most Current Status |
| Pressure Ulcer | L Heel | C | 3 | F | 61 | 12.29 | Healed |

| | Brief Medical History DOB Oct. 17, 1941 Unable to care for self at home | | | | | | |
|---|---|---|---|---|---|---|---|
| Date of Treatment | Patient wound history and clinic encounter | Wound Dimensions in cm Height | Width | Depth | cm₃ Dimensions | Healing % | Number of days Under Treatment |
| Jun. 27, 2005 | Treatment continuing | 6.00 | 0.50 | 0.01 | 0.03 | 99.25% | 69 |
| Apr. 19, 2005 | RTD applied | 8.00 | 2.50 | 0.20 | 4.00 | — | — |

*When the wound is flat, but not covered with skin, depth is arbitrarily determined to be 0.01 cm for purposes of cm₃ calculation. When wound is covered with new skin the depth is 0.00

| 20050423 Wound 16 | | | | | | | |
|---|---|---|---|---|---|---|---|
| Wound Type | Loca-tion | Acute Chronic | Stage | Patient Gender | Age | Weeks in Study | Most Current Status |
| Pressure Ulcer | R Heel | C | 3 | F | 61 | 12.29 | Healed |

| | Brief Medical History DOB Jun. 21, 1943 Rheumatoid arthritis and obesity - Developed leg wound June 2004 - Biopsy results not yet know - preliminary diagnosis is pyoderma gangrenosum | | | | | | |
|---|---|---|---|---|---|---|---|
| Date of Treatment | Patient wound history and clinic encounter | Wound Dimensions in cm Height | Width | Depth | cm₃ Dimensions | Healing % | Number of days Under Treatment |
| Jul. 27, 2005 | Treatment continuing | 1.50 | 3.90 | 0.20 | 1.17 | 98.31% | 86 |
| May 02, 2005 | RTD applied | 5.50 | 7.00 | 1.80 | 69.30 | — | — |

*When the wound is flat, but not covered with skin, depth is arbitrarily determined to be 0.01 cm for purposes of cm₃ calculation. When wound is covered with new skin the depth is 0.00

Brief Medical History
DOB Jun. 21, 1943
Rheumatoid arthritis and obesity - Developed leg wound June 2004 - Biopsy results not yet known - preliminary diagnosis is pyoderma gangrenosum

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 27, 2005 | Treatment continuing | 2.00 | 2.00 | 0.30 | 1.20 | 91.98% | 86 |
| May 02, 2005 | RTD applied | 4.30 | 5.80 | 0.60 | 14.96 | — | — |

\* When the wound is flat, but not covered with skin, depth is arbitrarily determined to be 0.01 cm for purposes of $cm_3$ calculation. When wound is covered with new skin the depth is 0.00

20050425 Wound 18

| Wound Type | Location | Acute Chronic | Stage | Patient Gender | Age | Weeks in Study | Most Current Status |
|---|---|---|---|---|---|---|---|
| Pressure Ulcer | L Heel | C | 2 | M | 76 | 11.71 | Healed |

20050509 Wound 20

| Wound Type | Location | Acute Chronic | Stage | Patient Gender | Age | Weeks to Healing | Most Current Status |
|---|---|---|---|---|---|---|---|
| Pressure Ulcer | Coccyx | C | 1 | M | 65 | 2.00 | Healed |

Brief Medical History
DOB Jan. 17, 1929
Patient in constant pain

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 15, 2005 | Healed | 0.00 | 0.00 | 0.00 | 0.00 | 100.00% | 82 |
| Apr. 25, 2005 | Applied RTD | 0.80 | 0.80 | 0.20 | 0.13 | — | — |

\* When the wound is flat, but not covered with skin, depth is arbitrarily determined to be 0.01 cm for purposes of $cm_3$ calculation. When wound is covered with new skin the depth is 0.00

20050504 Wound 19

| Wound Type | Location | Acute Chronic | Stage | Patient Gender | Age | Weeks in Study | Most Current Status |
|---|---|---|---|---|---|---|---|
| Pressure Ulcer | R Heel | C | 2 | M | 52 | 10.29 | Healed |

DOB Jul. 19, 1952
Paraplegic in otherwise good health

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 15, 2005 | Healed - Eucerin only recommended | 0.00 | 0.00 | 0.00 | 0.00 | 100.00% | 72 |
| May 04, 2005 | RTD applied | 3.00 | 5.00 | 0.20 | 3.00 | — | — |

\* When the wound is flat, but not covered with skin, depth is arbitrarily determined to be 0.01 cm for purposes of $cm_3$ calculation. When wound is covered with new skin the depth is 0.00

| | Brief Medical History DOB May 05, 1940 | | | | | | |
|---|---|---|---|---|---|---|---|
| Date of Treatment | Patient wound history and clinic encounter | Wound Dimensions in cm | | | cm₃ Dimensions | Healing % | Number of days Under Treatment |
| | | Height | Width | Depth | | | |
| May 23, 2005 | Healed | 0.00 | 0.00 | 0.00 | 0.00 | 100.00% | 14 |
| May 09, 2005 | Clean | 1.20 | 1.20 | 0.10 | 0.14 | — | — |

* When the wound is flat, but not covered with skin, depth is arbitrarily determined to be 0.01 cm for purposes of cm₃ calculation. When wound is covered with new skin the depth is 0.00

| 20050518 Wound 21 | | | | | | | |
|---|---|---|---|---|---|---|---|
| Wound Type | Location | Acute Chronic | Stage | Patient Gender | Age | Weeks in Study | Most Current Status |
| Pressure Ulcer | R Heel | C | 3 | M | 70 | 7.14 | Healed |

| | Brief Medical History DOB Feb. 02, 1935 Mental retardation, persistent atrial flutter chronic renal insufficiency, diabetes, chronic urinary tract infection, chronic anemia | | | | | | |
|---|---|---|---|---|---|---|---|
| Date of Treatment | Patient wound history and clinic encounter | Wound Dimensions in cm | | | cm₃ Dimensions | Healing % | Number of days Under Treatment |
| | | Height | Width | Depth | | | |
| Jul. 07, 2005 | healed | 0.00 | 0.00 | 0.00 | 0.00 | 100.00% | 50 |
| May 18, 2005 | Bleeding at wound site and at tumor removal incision which is on a wound pump | 5.00 | 4.00 | 0.10 | 2.00 | — | — |

* When the wound is flat, but not covered with skin, depth is arbitrarily determined to be 0.01 cm for purposes of cm₃ calculation. When wound is covered with new skin the depth is 0.00

| 20050624 Wound 22 | | | | | | | |
|---|---|---|---|---|---|---|---|
| Wound Type | Location | Acute Chronic | Stage | Patient Gender | Age | Weeks in Study | Most Current Status |
| Pressure Ulcer | Coccyx | C | 2 | M | 30 | 4.14 | Healed |

Brief Medical History
DOB Jun. 08, 1975
Long term history of seizures with mental impairment and developmental delay, incomplete quadrapelegia, recurrent urinary tract infections.

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 22, 2005 | Healed | 0.00 | 0.00 | 0.00 | 0.00 | 100.00% | 28 |
| Jun. 24, 2005 | RTD applied | 1.00 | 3.50 | 0.60 | 2.10 | — | — |

\* When the wound is flat, but not covered with skin, depth is arbitrarily determined to be 0.01 cm for purposes of $cm_3$ calculation. When wound is covered with new skin the depth is 0.00

20050624 Wound 23

| Wound Type | Location | Acute Chronic | Stage | Patient Gender | Age | Weeks in Study | Most Current Status |
|---|---|---|---|---|---|---|---|
| Pressure Ulcer | L Buttocks | C | 1 | M | 30 | 4.43 | Healed |

20050624 Wound 25

| Wound Type | Location | Acute Chronic | Stage | Patient Gender | Age | Weeks in Study | Most Current Status |
|---|---|---|---|---|---|---|---|
| Pressure Ulcer | Coccyx Crease | C | 2 | M | 30 | 14.00 | In process |

Brief Medical History
DOB Jun. 08, 1975
Long term history of seizures with mental impairment and developmental delay, incomplete quadrapelegia, recurrent urinary tract infections.

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 29, 2005 | Healed | 0.00 | 0.00 | 0.00 | 0.00 | 100.00% | 35 |
| Jun. 24, 2005 | RTD applied | 3.00 | 1.50 | 0.05 | 0.23 | — | — |

\* When the wound is flat, but not covered with skin, depth is arbitrarily determined to be 0.01 cm for purposes of $cm_3$ calculation. When wound is covered with new skin the depth is 0.00

20050624 Wound 24

| Wound Type | Location | Acute Chronic | Stage | Patient Gender | Age | Weeks in Study | Most Current Status |
|---|---|---|---|---|---|---|---|
| Pressure Ulcer | R Buttocks | C | 1 | M | 30 | 2.86 | Healed |

Brief Medical History
DOB Jun. 08, 1975
Long term history of seizures with mental impairment and developmental delay, incomplete quadrapelegia, recurrent urinary tract infections.

| Date of Treatment | Patient wound history and clinic encounter | Wound Dimensions in cm | | | $cm_3$ Dimensions | Healing % | Number of days Under Treatment |
|---|---|---|---|---|---|---|---|
| | | Height | Width | Depth | | | |
| Jul. 22, 2005 | Healed | 0.00 | 0.00 | 0.00 | 0.00 | 100.00% | 19 |
| Jun. 24, 2005 | RTD applied | 6.00 | 2.40 | 0.01 | 0.14 | — | — |

\* When the wound is flat, but not covered with skin, depth is arbitrarily determined to be 0.01 cm for purposes of $cm_3$ calculation. When wound is covered with new skin the depth is 0.00

Brief Medical History
DOB Jun. 08, 1975
Long term history of seizures with mental impairment and developmental delay, incomplete quadrapelegia, recurrent urinary tract infections.

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Sep. 30, 2005 | Treatment continuing | 5.50 | 2.4 | 0.01 | 0.13 | 93.71% | 98 |
| Jun. 24, 2005 | RTD and adaptic applied | 3.50 | 1.00 | 0.60 | 2.10 | — | — |

* When the wound is flat, but not covered with skin, depth is arbitrarily determined to be 0.01 cm for purposes of cm₃ calculation. When wound is covered with new skin the depth is 0.00

20050811 Wound 26

| Wound Type | Location | Acute Chronic | Stage | Patient Gender | Age | Weeks in Study | Most Current Status |
|---|---|---|---|---|---|---|---|
| Pressure Ulcer | L Heel | C | 1 | F | 78 | 6.29 | Healed |

Brief Medical History
DOB Mar. 26, 1927
Hypertensive, with cerebellar atrophy, GERD

| Date of Treatment | Patient wound history and clinic encounter | Wound Dimensions in cm | | | cm₃ Dimensions | Healing % | Number of days Under Treatment |
|---|---|---|---|---|---|---|---|
| | | Height | Width | Depth | | | |
| Sep. 01, 2005 | Healed | 0.00 | 0.00 | 0.00 | 0.00 | 100.00% | 44 |
| Jul. 19, 2005 | Part of a 2.3 × 2.3 ulcer adaptic and RTD applied | 1.50 | 1.50 | 0.10 | .23 | — | — |

* When the wound is flat, but not covered with skin, depth is arbitrarily determined to be 0.01 cm for purposes of cm₃ calculation. When wound is covered with new skin the depth is 0.00

20050922 Wound 27

| Wound Type | Location | Acute Chronic | Stage | Patient Gender | Age | Weeks in Study | Most Current Status |
|---|---|---|---|---|---|---|---|
| Pressure Ulcer | L Foot Dorsum | C | 1 | M | 67 | 1.57 | Healed |

| Brief Medical History<br>DOB Sep. 19, 1938<br>Diabetes onset 1990 - Recently diagnosed with CHF - lasix and insulin ||||||||
|---|---|---|---|---|---|---|---|
| Date of Treatment | Patient wound history and clinic encounter | Wound Dimensions in cm ||| cm₃ Dimensions | Healing % | Number of days Under Treatment |
| | | Height | Width | Depth | | | |
| Oct. 14, 2005 | Healed | 0.00 | 0.00 | 0.00 | 0.00 | 100.00% | 11 |
| Oct. 03, 2005 | RTD applied | 1.00 | 0.50 | 0.10 | 0.05 | — | — |

* When the wound is flat, but not covered with skin, depth is arbitrarily determined to be 0.01 cm for purposes of cm₃ calculation. When wound is covered with new skin the depth is 0.00

Our overall average for pressure ulcer on 12 week timelines to healing taken from the preceding tables:

| Wound Number | Healing percentage @ 12 weeks |
|---|---|
| 1 | 87.50% |
| 2 | 86.67% |
| 3 | 100.00% |
| 4 | 98.57% |
| 5 | 100.00% |
| 6 | 100.00% |
| 7 | 54.89% |
| 8 | 42.13% |
| 9 | 100.00% |
| 10 | 100.00% |
| 11 | 100.00% |
| 12 | 100.00% |
| 13 | 97.16% |
| 14 | 92.82% |
| 15 | 98.31% |
| 16 | 91.98% |
| 17 | 100.00% |
| 18 | 100.00% |
| 19 | 100.00% |
| 20 | 100.00% |
| 21 | 100.00% |
| 22 | 100.00% |
| 23 | 100.00% |
| 24 | 100.00% |
| 25 | 93.71% |
| 26 | 100.00% |
| 27 | 100.00% |
| Average Rate | 91.97% |

An invention has been provided with several advantages. The dressings of the invention are formed primarily from medical-grade hydrophilic urethanes and utilize ingredients with low absorption rates of mammal proteins. Specifically, the preferred form of the invention may use polyethyleneglycol as one of the significant ingredients. The wound dressing-treatment pads of the invention effectively absorb, by capillary action, the skin-wound exudate (fluid), while leaving intact the regenerative skin building proteins. Any microbe-infected liquid is removed from the wound surface, thus enabling healing to occur faster, with minimal potential scarring. The wound exudate saturates the edge of the skin growth, causing it to swell (like skin soaked too long in water), which inhibits skin growth. The exudate absorption action of the hydrophilic foam removes this disruptive excess fluid from the wounds growth zone, significantly reduces healing zone swelling, and thus encourages blood flow with faster healing.

The undesirable microbes which are present at the wound site are removed from the flesh's healing zone and surface. The pathogens suspended within the absorbed fluids are "externally" killed by effective organic/inorganic anti-microbial agents within the porosity of the capillary foam dressing. As a result of this action: (a) the wound remains germ free, such that the skin growth process does not have to compete with microbes for bodily nutrients; and (b) the microbes are withdrawn from the body and killed within the disposable foam structure. The absorbed germs cannot survive and mutate within the body to become resistant to medicines, such that the effectiveness of the dressing's system is preserved; the germ's susceptibility to the functional medicines are preserved by their removal outside the body into a disposable, external kill-zone.

Applicant's wound dressing treatments may be applied by non-medical staff without training and without prescription. The dressings do not inherently "stick" to wounds, by virtue of the hydrophilic nature of the foams utilized, as well as the specific combination of organic and/or inorganic antimicrobials utilized.

As has been explained, the particular choice of active agents which are incorporated into the foams of the invention produces a synergistic effect which works to stimulate blood-flow, which results in faster than normal wound healing. A number of factors act together to achieve faster than normal healing compared to traditional wound dressings or bandages. Mammal skin is weakened by submersion in liquids with the result that maceration occurs. The dressings of the invention prevent maceration by wicking/sucking away the excess liquid, while leaving proper moisture without drying, so as to encourage skin growth, without scabbing.

The application of the wound dressing-treatments of the invention to actual patients indicates that user patients experience a measurably reduced to almost extinguished level of pain. The discomfort of pain from skin-burns or skin-wounds is significantly reduced, to virtually eliminated, within 30 minutes to 24 hours after the application of the pads of the invention, depending upon severity, size, and age of the wound. User patients report a "cooling" sensation shortly after application of this wound care device. This is interpreted as immediate removal of saprophytic microbes and encouragement of blood-flow to the injured area, resulting in tissue nourishment, tissue growth, skin re-granulation, and healing, virtually upon its application to the wounded area. The wound dressings of the invention also provide the ability to reduce and inhibit significant skin "scarring" from wounds. Wounds immediately treated with the dressing exhibit significantly reduced "scarring", to virtually no skin "scarring", depending upon the nature, depth, and severity of the wound.

The wound dressings of the invention are effective in preserving the susceptibility of infectious pathogens to the above named organic/inorganic antimicrobials. By inhibiting growth and even killing microbes, fungi, and virus outside the body, followed by disposal of the used pad, the infectious pathogens cannot mutate and reproduce to acquire or develop resistance to these organic/inorganic antimicrobials. Thus, the infectious pathogens gain no immunity or resistance, and remain susceptible to antimicrobial treatment. The dressing remains toxic to exposed pathogens.

The application of the dressings of the invention does not require trained or licensed medical personnel. This encourages home-care versus expensive medical hospitalization. Its use requires only a "clean" environment, not a "sterile" environment. The wound dressing of the invention can be used to treat many skin wounds including, but not limited to: surgery incisions, skin cuts/scrapes, dermal ulcers, diabetic ulcers, bed-sores, shingles, punctures, herpes, burns, ambulatory amputee stump wounds, veterinary uses, pressure ulcerations, spinal cord injury, donor sites, skin grafts, first and second degree burns, venous-stasis ulcer, vascular access sites, abrasions and lacerations.

While the invention has been shown in several of its forms, it is not thus limited but is susceptible to various changes and modifications without departing from the spirit thereof. The preferred formulation using in-organic anti-microbials is as given in this patent, but, to those skilled in the art, the antimicrobial formulation itself does not exclude future formulations to include physician prescribed organic antimicrobials (such as cyclosporin); and while the present formulation exhibits an inherent wound pain relief, future formulations may include supplemental prescription, or non-prescription, wound-pain relievers (such as lanacaine and other substances).

What is claimed is:

1. A wound treatment-dressing, comprising:
   a dressing body having at least a wound contacting surface layer which is formed from a hydrophilic, capillary active, medically inert, moisture permeable, urethane open-cell foam which provides conformational area contact over the wound treatment area without local non-contact;
   wherein the foam which makes up at least the wound contacting surface of the dressing body exists as a foam matrix comprised of interconnected foam cells with cell walls which have incorporated therein a combination of inorganic antimicrobial particles as active agents, the active agents being incorporated into the foam matrix both protruding through the foam cell wall and integrally within the foam cell wall, whereby the foam functions by capillary and hydrophilic action as a liquid absorber with liquid exudate being absorbed from the wound treatment area into the foam matrix where it is retained against free flow out of the wound treatment-dressing and is kept away from the wound to facilitate healing, whereby microbial organisms are removed from the wound and killed in an external killing zone;
   wherein the particles which are encapsulated into the foam matrix consist of gentian-violet, methylene-blue and colloidal or ionic silver, wherein the gentian-violet and methylene-blue components are present in the foam matrix as nano-sized particles which range in spherical diameter from about 19 microns to 8000 microns, and wherein the dressing body having the previously described characteristics comprises a finished manufactured foam wound treatment-dressing which has an anti-microbial concentration of each of the gentian-violet, methylene-blue and colloidal or ionic silver components in the range from 0.0001% to 9% (gr/gr) by weight of each component; and
   wherein the dressing body which makes up the finished manufactured foam wound treatment-dressing has a thickness in the range from about 2 to 10 mm.

2. The wound treatment-dressing of claim 1, wherein the foam body has a volume absorbency ratio which is greater than about 20:1.

3. The wound treatment-dressing of claim 1, wherein a given weight percentage of each antimicrobial agent in the form of particles is physically mixed into a solution of polymer foam ingredients prior to foaming, such that the antimicrobials are mechanically included in the foam cell wall upon foaming, whereby some quantity of antimicrobial particles will be totally encapsulated into the interconnected foam cells with a remaining quantity protruding through the foam cell walls to be physically exposed into void space present in the open-foam cell.

4. The wound treatment-dressing of claim 3, wherein the antimicrobial particles are not deposited onto the cell wall, but are physically included within and physically protruding from the cell wall.

5. a wound treatment comprising:
   a dressing body having at least a wound contacting surface layer which is formed from a hydrophilic, capillary active, medically inert, moisture permeable, urethane open-cell foam which provides conformational area contact over the wound treatment area without local non-contact;
   wherein the foam which makes up at least the wound contacting surface of the dressing body exists as a foam matrix comprised of interconnected foam cells with cell walls which have incorporated therein a combination of inorganic antimicrobial particles as active agents, the active agents being incorporated into the mechanically active foam matrix both protruding from the foam cell surface and integrally within the foam cell wall, whereby the foam functions as a liquid absorber with liquid exudate being absorbed from the wound treatment area into the foam matrix where it is retained against free flow out of the wound treatment-dressing and is kept away from the wound to facilitate healing, whereby microbial organisms are removed from the wound and killed in an external killing zone;
   wherein the open-cell foam is made by the steps of:
   physically mixing a given weight percentage of each antimicrobial agent, in the form of particles, into a solution of polymer foam ingredients prior to foaming; and
   producing a finished manufactured foam wound treatment-dressing from the polymer foam ingredients, including the antimicrobial agents, in a foaming step such that the antimicrobials are mechanically included in the foam cell wall upon foaming, whereby some quantity of antimicrobial particles will be totally encapsulated into the wall's interconnected foam cells with a remaining quantity protruding through the foam cell walls to be physically exposed into the void space of present in the open-foam cell, the incorporation of the antimicrobial particles during the foaming step resulting in the antimicrobial particles being physically captured and no longer mobile;
   wherein the particles which are encapsulated into the foam matrix of consist [essentially] of gentian-violet, methylene-blue and colloidal or ionic silver, wherein the gentian-violet and methylene-blue components are present in the foam matrix as nano-sized particles which range in spherical diameter from about 19 microns to 8000 microns, manufactured foam wound treatment-dressing which has an antimicrobial concentration of each of the gentian-violet, methylene-blue and colloidal or ionic silver components in the range from 0.0001% to 9% (gr/gr) by weight of each component; and wherein the foam dressing body which makes up the finished manufactured foam wound treatment-dressing has a thickness in the range from about 2 to 10 mm.

6. The wound treatment-dressing of claim 5, wherein the colloidal or ionic silver which is incorporated into the foam matrix is a zirconium phosphate ceramic ion-exchange resin containing silver in the form of silver ions which slowly releases silver ions via an ion exchange mechanism.

7. The wound treatment-dressing of claim 6, wherein the particles which are encapsulated within the foam matrix are made by a method which further comprises the steps of:

manufacturing nano-sized antimicrobial particles for incorporation into the foam matrix by first solvating gentian-violet or methylene-blue into a warm solvent at the thermal saturation limit;

thereafter, pressure spraying the concentrated solution through a droplet atomizing nozzle such that tiny uniform droplets of hot concentrated solution are ejected into a vacuum chamber where the solvent flashes, leaving tiny, uniform solid crystal particles at the chamber bottom;

thereafter, evacuating the solvent gas via vacuum pump, and removing the resulting nano-sized antimicrobial particles.

8. The wound treatment-dressing of claim 7, wherein the dressing body which makes up the finished manufactured foam wound treatment-dressing has a thickness in the range of about 3 to 7 mm.

* * * * *

UNITED STATES PATENT AND TRADEMARK OFFICE
CERTIFICATE OF CORRECTION

| | |
|---|---|
| PATENT NO. | : 8,227,656 B2 |
| APPLICATION NO. | : 12/658530 |
| DATED | : July 24, 2012 |
| INVENTOR(S) | : Harvey E. Svetlik |

It is certified that error appears in the above-identified patent and that said Letters Patent is hereby corrected as shown below:

Column 1, lines 7-12, cancel the text beginning with "The present application claims priority from" to and ending with "by Harvey E. Svetlik," and insert the following:

--The present application is a divisional of prior application Serial No. 11/368,127, filed March 3, 2006, entitled "Wound Treatment Dressing and Method of Manufacture," by Harvey E. Svetlik.--

Signed and Sealed this
Fifteenth Day of January, 2013

David J. Kappos
*Director of the United States Patent and Trademark Office*